United States Patent
Campbell et al.

(10) Patent No.: US 10,130,466 B2
(45) Date of Patent: Nov. 20, 2018

(54) PRE-ASSEMBLED BIOPROSTHETIC VALVE CONDUIT AND METHOD OF DELIVERY

(71) Applicant: Edwards Lifesciences Corporation, Irvine, CA (US)

(72) Inventors: Louis A. Campbell, Santa Ana, CA (US); Donald E. Bobo, Jr., Santa Ana, CA (US); Gregory A. Wright, Orange, CA (US); Tak G. Cheung, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 65 days.

(21) Appl. No.: 15/079,854

(22) Filed: Mar. 24, 2016

(65) Prior Publication Data
US 2016/0270913 A1    Sep. 22, 2016

Related U.S. Application Data

(63) Continuation of application No. 13/906,166, filed on May 30, 2013, now Pat. No. 9,301,835.
(Continued)

(51) Int. Cl.
*A61F 2/24* (2006.01)
*A61L 27/36* (2006.01)
(Continued)

(52) U.S. Cl.
CPC .......... *A61F 2/2418* (2013.01); *A61F 2/0095* (2013.01); *A61F 2/06* (2013.01);
(Continued)

(58) Field of Classification Search
CPC ........ A61F 2/24; A61F 2/2448; A61F 2/2445; A61F 2/2412; A61F 2/2418
(Continued)

(56) References Cited

U.S. PATENT DOCUMENTS

| 512,391 A | 1/1894 | Rolando et al. |
|---|---|---|
| 3,997,923 A | 12/1976 | Possis |

(Continued)

FOREIGN PATENT DOCUMENTS

| EP | 0169259 A1 | 1/1986 |
|---|---|---|
| EP | 2478871 A2 | 7/2012 |

(Continued)

OTHER PUBLICATIONS

Maselli, et al., "Adjustable Sinotubular Junction for Aortic Valve Reimplantation Procedures", Cardiothoracic Department, Azienda Ospedaliera Universitaria Pisana, Pisa, Italty, The Society of Thoracic Surgeons, Published by Elsevier Inc, 200, pp. 700-702.

*Primary Examiner* — Suzette J Gherbi
(74) *Attorney, Agent, or Firm* — Thomas C. Richardson

(57) ABSTRACT

A valved conduit including a bioprosthetic valve, such as a heart valve, and a tubular conduit sealed with a bioresorbable material. The bioprosthetic heart valve includes prosthetic tissue that has been treated such that the tissue may be stored dry for extended periods without degradation of functionality of the valve. The bioprosthetic heart valve may have separate bovine pericardial leaflets or a whole porcine valve. The sealed conduit includes a tubular matrix impregnated with a bioresorbable medium such as gelatin or collagen. The valved conduit is stored dry in packaging in which a desiccant pouch is supplied having a capacity for absorbing moisture within the packaging limited to avoid drying the bioprosthetic tissue out beyond a point where its ability to function in the bioprosthetic heart valve is compromised. The heart valve may be sewn within the sealed conduit or coupled thereto with a snap-fit connection.

17 Claims, 10 Drawing Sheets

Related U.S. Application Data

(60) Provisional application No. 61/655,405, filed on Jun. 4, 2012.

(51) Int. Cl.
*A61F 2/00* (2006.01)
*A61F 2/06* (2013.01)
*A61L 27/22* (2006.01)
*A61L 27/24* (2006.01)
*A61L 27/50* (2006.01)

(52) U.S. Cl.
CPC .......... *A61F 2/2409* (2013.01); *A61F 2/2412* (2013.01); *A61F 2/2415* (2013.01); *A61F 2/2427* (2013.01); *A61L 27/222* (2013.01); *A61L 27/24* (2013.01); *A61L 27/3625* (2013.01); *A61L 27/3687* (2013.01); *A61L 27/507* (2013.01); *A61F 2210/0004* (2013.01); *A61F 2220/0075* (2013.01); *A61F 2310/00371* (2013.01); *A61F 2310/00383* (2013.01); *A61L 2430/20* (2013.01); *A61L 2430/40* (2013.01)

(58) Field of Classification Search
USPC .................................. 623/2.1–2.19
See application file for complete search history.

(56) References Cited

U.S. PATENT DOCUMENTS

| | | | |
|---|---|---|---|
| 4,182,446 A * | 1/1980 | Penny | A61F 2/0095 206/205 |
| 4,218,782 A | 8/1980 | Rygg | |
| 4,692,164 A | 9/1987 | Dzemeshkevich et al. | |
| 4,747,848 A | 5/1988 | Maini | |
| 5,123,919 A | 6/1992 | Sauter et al. | |
| 5,139,515 A | 8/1992 | Robicsek | |
| 5,197,979 A | 3/1993 | Quintero et al. | |
| 5,376,112 A | 12/1994 | Duran | |
| 5,545,215 A | 8/1996 | Duran | |
| 5,814,096 A | 9/1998 | Lam et al. | |
| 5,862,806 A | 1/1999 | Cheung | |
| 5,891,195 A | 4/1999 | Klostermeyer et al. | |
| 5,910,169 A * | 6/1999 | Peredo | A61F 2/2412 623/2.1 |
| 6,001,126 A | 12/1999 | Nguyen-Thien-Nhon | |
| 6,090,140 A | 7/2000 | Gabbay | |
| 6,254,635 B1 * | 7/2001 | Schroeder | A61L 27/042 623/2.13 |
| 6,264,691 B1 | 7/2001 | Gabbay | |
| 6,299,638 B1 | 10/2001 | Sauter | |
| 6,352,554 B2 | 3/2002 | De Paulis | |
| 6,390,447 B1 | 5/2002 | Mosher | |
| 6,482,228 B1 | 11/2002 | Norred | |
| 6,524,339 B1 * | 2/2003 | Adams | A61F 2/2412 623/2.13 |
| 6,783,556 B1 | 8/2004 | Gabbay | |
| 6,875,230 B1 | 4/2005 | Morita et al. | |
| 6,976,952 B1 | 12/2005 | Maini et al. | |
| 7,018,404 B2 | 3/2006 | Holmberg et al. | |
| 7,261,732 B2 | 8/2007 | Justino | |
| 7,316,712 B2 * | 1/2008 | Peredo | A61F 2/2412 623/2.13 |
| 7,422,603 B2 | 9/2008 | Lane | |
| 7,488,346 B2 | 2/2009 | Navia | |
| 7,575,592 B2 | 8/2009 | Woo | |
| 7,618,447 B2 | 11/2009 | Case et al. | |
| 7,625,403 B2 | 12/2009 | Krivoruchko | |
| 7,641,686 B2 | 1/2010 | Lashinski et al. | |
| 7,641,687 B2 | 1/2010 | Chinn et al. | |
| 7,686,844 B2 | 3/2010 | Case et al. | |
| 7,717,952 B2 | 5/2010 | Case et al. | |
| 7,806,920 B2 | 10/2010 | Duran | |
| 7,972,376 B1 | 7/2011 | Dove et al. | |
| 8,080,054 B2 | 12/2011 | Rowe | |
| 9,289,282 B2 | 3/2016 | Olson et al. | |
| 9,301,835 B2 * | 4/2016 | Campbell | A61F 2/2412 |
| 9,498,317 B2 | 11/2016 | Gautam et al. | |
| 9,585,748 B2 | 3/2017 | Wright | |
| 9,801,711 B2 * | 10/2017 | Gainor | A61F 2/2412 |
| 2003/0139805 A1 | 7/2003 | Holmberg et al. | |
| 2003/0187500 A1 | 10/2003 | Jansen et al. | |
| 2004/0193242 A1 | 9/2004 | Lentz et al. | |
| 2005/0055079 A1 * | 3/2005 | Duran | A61F 2/2412 623/1.13 |
| 2005/0113910 A1 | 5/2005 | Paniagua et al. | |
| 2005/0143810 A1 | 6/2005 | Dauner et al. | |
| 2005/0222675 A1 | 10/2005 | Sauter | |
| 2005/0267559 A1 | 12/2005 | De Oliveira | |
| 2006/0085060 A1 | 4/2006 | Campbell | |
| 2006/0167386 A1 | 7/2006 | Drake et al. | |
| 2006/0271081 A1 | 11/2006 | Realyvasquez | |
| 2007/0084144 A1 * | 4/2007 | Labrecque | A61L 2/07 53/425 |
| 2007/0213813 A1 * | 9/2007 | Von Segesser | A61F 2/2418 623/2.18 |
| 2007/0219630 A1 * | 9/2007 | Chu | A61F 2/2412 623/2.11 |
| 2007/0233237 A1 | 10/2007 | Krivoruchko | |
| 2008/0082161 A1 * | 4/2008 | Woo | A61F 2/0095 623/1.26 |
| 2008/0147171 A1 | 6/2008 | Ashton et al. | |
| 2009/0093873 A1 | 4/2009 | Navia | |
| 2009/0264993 A1 | 10/2009 | Greenan | |
| 2010/0249894 A1 * | 9/2010 | Oba | A61F 2/2418 623/1.11 |
| 2010/0274351 A1 | 10/2010 | Rolando et al. | |
| 2011/0214398 A1 | 9/2011 | Liburd et al. | |
| 2011/0264201 A1 | 10/2011 | Yeung et al. | |
| 2011/0301688 A1 | 12/2011 | Dolan | |
| 2012/0009551 A1 | 1/2012 | Pinnisi | |
| 2012/0010697 A1 | 1/2012 | Shin et al. | |
| 2012/0046726 A1 | 2/2012 | Chuter | |
| 2012/0046738 A1 * | 2/2012 | Lau | A61F 2/2412 623/2.1 |
| 2012/0132547 A1 | 5/2012 | Salahieh et al. | |
| 2013/0325111 A1 * | 12/2013 | Campbell | A61F 2/2412 623/2.11 |
| 2014/0121764 A1 * | 5/2014 | De Paulis | A61F 2/06 623/2.11 |
| 2014/0330367 A1 * | 11/2014 | Thapliyal | A61F 2/2415 623/2.11 |
| 2015/0064140 A1 * | 3/2015 | Kassab | A61L 31/08 424/93.7 |
| 2016/0067042 A1 * | 3/2016 | Murad | A61F 2/2409 623/2.17 |
| 2016/0081829 A1 | 3/2016 | Rowe | |
| 2016/0128829 A1 * | 5/2016 | Oba | A61F 2/2418 623/2.11 |
| 2016/0266004 A1 | 9/2016 | Van Nest et al. | |

FOREIGN PATENT DOCUMENTS

| | | |
|---|---|---|
| WO | 9958082 A2 | 11/1999 |
| WO | 03007795 A2 | 1/2003 |
| WO | 2006/013234 A1 | 2/2006 |
| WO | 2011109630 A2 | 9/2011 |

* cited by examiner

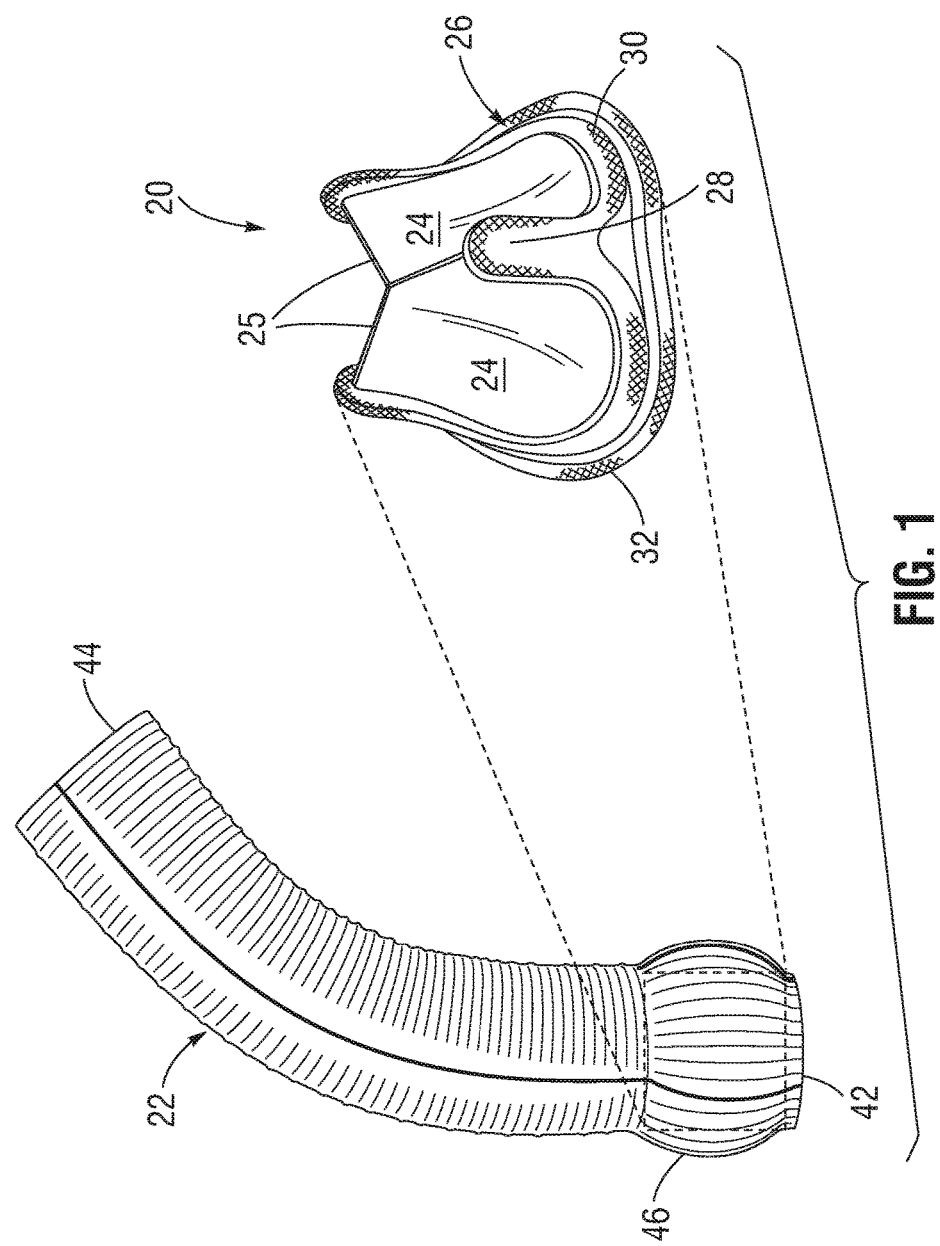

PRE-ASSEMBLED BIOPROSTHETIC VALVE CONDUIT AND METHOD OF DELIVERY

CROSS REFERENCE TO RELATED APPLICATIONS

This application is a continuation of U.S. patent application Ser. No. 13/906,166, filed May 30, 2013, which claims the benefit of U.S. patent application Ser. No. 61/655,405, filed Jun. 4, 2012, the entire disclosures all of which are incorporated by reference.

FIELD OF THE INVENTION

The present invention generally relates to prosthetic heart valves assembled with a flow conduit and, more particularly, to a pre-assembled bioprosthetic heart valve and sealed conduit.

BACKGROUND OF THE INVENTION

Heart valve disease continues to be a significant cause of morbidity and mortality, resulting from a number of ailments including rheumatic fever and birth defects. Cardiovascular disease is the number one cause of death, killing more than 600,000 Americans each year. According to the American Heart Association, more than five million Americans are diagnosed with heart valve disease each year. Heart valve disease can occur in any single valve or a combination of the four valves, but diseases of the aortic and mitral valves are the most common, affecting more than five percent of the population. An estimated 85,000 aortic valve replacement procedures are performed every year in the U.S. Worldwide, approximately 300,000 heart valve replacement surgeries are performed annually. About one-half of these patients receive bioprosthetic heart valve replacements, which utilize biologically derived tissues for flexible fluid occluding leaflets.

The most successful bioprosthetic materials for flexible leaflets are whole porcine valves and separate leaflets made from bovine pericardium stitched together to form a tri-leaflet valve. The most common flexible leaflet valve construction includes three leaflets mounted to commissure posts around a peripheral support structure with free edges that project toward an outflow direction and meet or coapt in the middle of the flowstream. A suture-permeable sewing ring is provided around the inflow end. Various tissue treatments extend the life of the heart valve, such as by reducing calcification, thus deferring the need for a second surgery to replace the first implanted valve. The use of glutaradehyde in such tissue treatments has been proven effective in avoiding resorption of the treated tissue after implantation.

Bioprosthetic heart valves are conventionally packaged in jars filled with preserving solution for shipping and storage prior to use in the operating theater. The preserving solution maintains the functionality of the bioprosthetic tissue within the heart valve. Glutaraldehyde and formaldehyde are widely used as storage solutions due to their sterilant properties.

Prosthetic heart valves may be implanted independently in one of the orifices or annuluses of the heart, or may be coupled to a flow conduit which extends in line with the valve a predetermined distance. For example, the Carpentier-Edwards® Bioprosthetic Valved Conduit available from Edwards Lifesciences of Irvine, Calif. features a porcine bioprosthetic heart valve to which are coupled both and inflow and outflow woven polyester extensions. The Edwards valved conduit is particularly well-suited for treatment of a malfunctioning pulmonic valve. Other valved conduits are designed for reconstruction of portions of the flow passage above and below the aortic valve, such as the ascending aorta, in addition to replacing the function of the valve itself. There are also other applications for valved conduits, such as to provide a bypass flow path connecting the apex of the heart directly to the descending aorta. Prior bioprosthetic valved conduits, as with bioprosthetic heart valves, are stored in a liquid preserving solution, and thus the conduits are formed of woven polyester without a bioresorbable sealant. Although such conduits are suitable in certain situations, and tend to seal relatively quickly in the body from tissue ingrowth, too much blood can initially seep through their walls after implant which may be detrimental. Uncoated fabric such as polyethylene terephthalate (PET) has a high leakage rate, and thus the surgeon needs to pre-clot the graft with patient's blood before use. Nevertheless, such grafts still produce unacceptable leaking. Others have proposed using a non-bioresorbable sealant layer, such as silicone in U.S. Patent Publication No. 2008/0147171 to Ashton, et al., published Jun. 19, 2008, but such layered conduits tend to be relatively thick walled and not very flexible, and so are not preferred.

Consequently, some surgeons prefer conduits or grafts in which porous tubular structures such as woven polyester (e.g., Dacron) are impregnated with bioresorbable materials such as gelatin, collagen or albumin. These conduits are not porous initially, and thus prevent blood loss, but the sealant medium eventually degrades by hydrolysis when exposed to water after implant and are replaced by natural tissue ingrowth. Gelatin in the graft can also be treated in such a way as to cause cross links to form between the amino groups present in the gelatin molecules, which renders the gelatin more resistant to hydrolysis. Methods of forming such grafts are seen in U.S. Pat. No. 4,747,848 to Maini, issued May 31, 1988.

Unfortunately, it is not possible to pre-assemble conduits or grafts sealed using bioresorbable materials with bioprosthetic heart valves because of storage complications. That is, the liquid sterilant in which tissue valves are stored will eventually wash the bioresorbable sealing medium (gelatin, collagen, albumin, etc.) out of the permeable conduit material. Because of the benefits of using sealed conduits or grafts and the positive attributes of bioprosthetic heart valves, some surgeons couple the two components together at the time of surgery—post-storage. That is, technicians in the operating theater connect the sealed conduit which has been stored dry to the bioprosthetic heart valve which has been stored wet. Such assemblies can be seen in U.S. Patent Publication No. 2010/0274351 to Rolando, et al., published Oct. 28, 2010, and in U.S. Pat. No. 7,575,592 to Woo, et al., issued Aug. 18, 2009. The sealed conduit may be sewn to the sewing ring of the bioprosthetic heart valve, or some other form of quick-connect coupling can be provided, such as seen in U.S. Patent Publication No. 2006/0085060 to Campbell, published Apr. 20, 2006. Although these assemblies are in theory the best of both worlds, the time and effort required to connect a sealed conduit with a bioprosthetic heart valve creates problems in the high-pressure environment of the cardiac operating theater. Adding to the complexity of the connection procedure, the biological valve must be kept damp to avoid degradation of the tissue, while the graft must be kept dry to avoid initiating hydrolysis. Further, prolonged exposure of the valve and conduit in the operating room prior to implantation increases the chance of infection. For aortic conduits, even a small leak in this connection can be fatal because the pressure is so high. So the implanting surgeon has to sew these components together quickly without any leaks.

Accordingly, there is a need for a valved conduit having a bioprosthetic tissue valve and a conduit or graft preferably sealed using a bioresorbable material which is simpler to prepare and deploy in the operating room.

SUMMARY OF THE INVENTION

The present application discloses a valved conduit including a bioprosthetic heart valve and a tubular conduit sealed with a bioresorbable material. The bioprosthetic heart valve includes prosthetic tissue that has been treated such that the tissue may be stored dry for extended periods without degradation of functionality of the valve. For example, the tissue may have been cross-linked using glutaraldehyde or other aldehyde containing agents, treated with a capping agent, and dehydrated with a glycerol solution. The bioprosthetic heart valve may have separate bovine pericardial leaflets or a whole porcine valve. The sealed conduit includes a tubular matrix impregnated with a bioresorbable medium such as gelatin or collagen. The valved conduit is stored dry in packaging in which a desiccant pouch is supplied having a capacity for absorbing moisture within the packaging limited to avoid drying the bioprosthetic tissue out beyond a point where its ability to function in the bioprosthetic heart valve is compromised. The heart valve may be sewn within the sealed conduit, sewn to the end of the conduit or coupled thereto with a snap-fit connection to limit handling of the two treated components and provide a hemostatic seal with minimal assembly complexity. In one embodiment, the bioprosthetic valve couples within the conduit such that the conduit extends on both ends of the valve to provide both inflow and outflow extensions.

Another aspect of the present application is a packaged valved conduit, including a bioprosthetic valve such as a heart valve having bioprosthetic tissue, the valve having been treated such that the tissue may be stored dry for extended periods without degradation of functionality of the valve. The bioprosthetic valve is coupled to a conduit sealed with a bioresorbable medium to provide the valved conduit. Packaging for the valved conduit has at least one sterile container in which the valved conduit is stored without a preserving solution. The packaging may comprise a dual layer packaging with the valved conduit sealed within an inner gas-permeable sterile barrier to enable gas sterilization and an outer gas-impermeable barrier to prevent long term oxidation of the bioprosthetic tissue. Desirably, the conduit comprises a tubular matrix impregnated with gelatin, and further including a desiccant pouch provided within the packaging having a capacity for absorbing moisture within the packaging limited to avoid drying the bioprosthetic tissue out beyond a point where its ability to function as a bioprosthetic valve is compromised.

A method of preparing and delivering a valved conduit is also disclosed which includes first procuring a pre-assembled valved conduit including a bioprosthetic valve having bioprosthetic tissue coupled to a conduit sealed with a bioresorbable medium, the valved conduit being stored in a dry package. The method then requires opening the dry package and removing the valved conduit, and delivering the valved conduit to an implantation site. The conduit is preferably secured to the bioprosthetic valve using sutures, but may alternatively be secured using a snap-fit connection. The bioprosthetic valve may be a heart valve with bovine pericardial leaflets, and the conduit is desirably a tubular matrix impregnated with gelatin or collagen. In one embodiment, the bioprosthetic valve couples within the conduit such that the conduit extends on both ends of the valve to provide both inflow and outflow extensions. The bioprosthetic tissue has preferably been cross-linked using glutaraldehyde or other aldehyde containing agents, treated with a capping agent, and dehydrated with a glycerol solution.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 1 is an exploded view of the combination of a bioprosthetic heart valve coupled to a sealed conduit of the present application;

DETAILED DESCRIPTION OF THE PREFERRED EMBODIMENTS

Figure 1A:
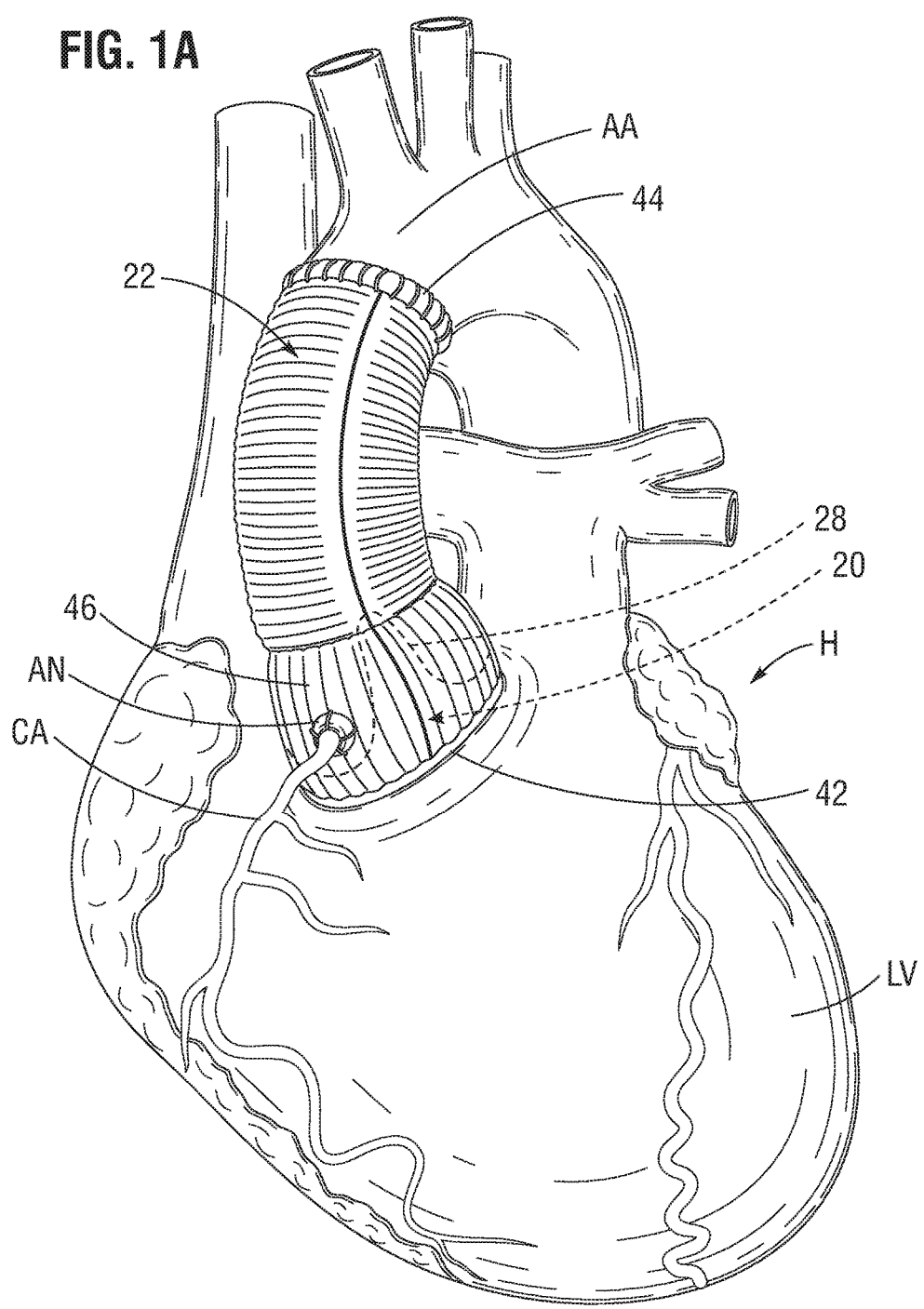
FIG. 1A is a view of a human heart showing implant of a valved conduit to replace the aortic valve and a portion of the ascending aorta.

The present application provides techniques for coupling implantable valves with sealed conduits, and in particular bioprosthetic heart valves that have been dried and are not stored immersed in a preservative solution. The term "dried" or "dry" bioprosthetic heart valves refers in general to the ability to store those heart valves without immersion in solution (e.g., a preservative like glutaraldehyde), and in particular to dry storage for extended periods without degradation of functionality of the bioprosthetic valve. There are a number of proposed methods for drying bioprosthetic heart valves, and for drying tissue implants in general, and the present application provides packaging for bioprosthetic heart valves that are processed by any of these methods.

One strategy for drying tissue is to dehydrate the bioprosthetic tissue in a glycerol/ethanol mixture, sterilize with ethylene oxide, and package the final product "dry." This process eliminates the potential toxicity of glutaraldehyde as a sterilant and storage solution. There have been several methods proposed to use sugar alcohols (i.e., glycerine), alcohols, and combinations thereof as post-glutaraldehyde processing methods so that the resulting tissue is in a "dry" state rather than a wet state with excess glutaraldehyde. Glycerol-based methods can be used for such storage, such as described in Parker et al. (Thorax 1978 33:638). A particularly preferred method of drying bioprosthetic heart valves is disclosed in U.S. Pat. No. 8,007,992 to Tian, et al. (the disclosure of which is expressly incorporated herein by reference) wherein fixed tissue is treated with a non-aqueous mixture of glycerol and $C_1$-$C_3$ alcohol selected from the group consisting of: methanol, ethanol, n-propanol, 2-propanol. Likewise, U.S. Pat. No. 6,534,004 (Chen et al.) describes the storage of bioprosthetic tissue in polyhydric alcohols such as glycerol. In processes where the tissue is dehydrated in an ethanol/glycerol solution, the tissue may be sterilized by ethylene oxide (ETO), gamma irradiation, or electron beam irradiation.

More recently, Dove, et al. in U.S. Pat. No. 7,972,376, issued Jul. 5, 2011, proposed solutions for certain detrimental changes within dehydrated tissue that can occur as a result of oxidation, the disclosure of which is expressly incorporated herein by reference. Dove, et al. propose permanent capping of the aldehyde groups in the tissue (reductive amination). One preferred anticalcification tissue treatment includes applying a calcification mitigant such as a capping agent or an antioxidant to the tissue to specifically inhibit oxidation in dehydrated tissue and reduce in vivo calcification. The treatment specifically caps aldehyde groups in crosslinked (e.g., with glutaraldehyde) bovine, porcine, or equine pericardial tissue or a porcine valve. In one method, tissue leaflets in assembled bioprosthetic heart valves are pretreated with an aldehyde capping agent prior to dehydration and sterilization. Dove, et al. also describe the addition of chemicals (e.g. antioxidants) to the dehydration solution (e.g., ethanol/glycerol) to prevent oxidation of the tissue during sterilization (ethylene oxide, gamma irradiation, electron beam irradiation, etc.) and storage. The capping process uses an amine, for example ethanolamine or lysine, and a reducing agent, followed by final processing with glycerol and an alcohol. The capping agent may be selected from the group consisting of: an amine, an amino acid, and an amino sulfonate. The reducing agent may be a borohydride, for example sodium borohydride or cyanoborohydyride. Other reducing agents include: sodium bisulfite+acetylacetone, and formic acid+formaldehyde.

These and other methods for drying bioprosthetic heart valves are used prior to coupling of the valve with the sealed conduit. The removal of a percentage of water from the valve and replacement with glycerol and ethanol allows the device to be stored "dry" (i.e. glycerolized). The "dry" valve may then be sewn into the polyester conduit or graft and be ready for implantation. This process allows making a valved conduit that is ready for implantation without the need for a clinical rinse in saline, thereby shortening implant time. For purpose of definition, a "dry" bioprosthetic tissue is one with less than 70% water content. In terms of practical rehydration, functional valves have at least 70% water content. The most important distinction of "dry" valves (or tissue therein), however, is that they may be stored dry for extended periods (sometimes years) without degradation of functionality of the valve.

A number of exemplary bioprosthetic heart valves and conduits are shown and described in the present application. Each of these different types of heart valves may be processed so that they are stored dry. The reader will understand that the present methodologies apply to any and all bioprosthetic valves that are stored dry, and are not limited to those exemplary valves shown herein. In particular, prosthetic heart valves for implant at any of the four native valve annuluses—aortic, mitral, pulmonary, and tricuspid—may be dried and stored in accordance with the principles described herein. Alternatively, valved conduits produced in accordance with the principles disclosed herein may be used in locations other than heart valve replacement, such as venous valves by connecting a small bileaflet valve to or within a small diameter conduit.

Additionally, a number of techniques for packaging the dry bioprosthetic heart valves and their delivery systems are illustrated and described herein, though these techniques can also apply to other packaging configurations. In general, a bioprosthetic heart valve must be stored in sterile conditions, which requires at least one sterile container. Preferably, however, a dual-barrier packaging system is used to reduce the chance of contamination of the implant at the time of surgery. For instance, U.S. Patent Publication No. 2011/0147251 to Hodson, et al. discloses exemplary packaging systems which can be utilized, the contents of which are hereby expressly incorporated herein.

The present application describes systems and methods for pre-assembling and storing a bioprosthetic heart valve and sealed conduit to form the valved conduit. The term "pre-assembling" or "pre-assembled" refers to connection of the heart valve and sealed conduit prior to the operating room technicians opening the sterile packaging. In other words, the valved conduit emerges mechanically assembled from the packaging, substantially ready for delivery (after any pre-surgery washing or other such preparation).

FIG. 1 is an exploded view of an exemplary combination of a bioprosthetic heart valve 20 coupled to a sealed conduit 22. As suggested schematically, the prosthetic heart valve 20 is positioned within one end of the sealed conduit 22. Such a valved conduit may be used for replacing a native heart valve and an associated blood vessel in a patient. The aortic valve and the ascending aorta are one non-limiting example of such a valve and an associated blood vessel. The pulmonary valve and the pulmonary artery are another such example.

The heart valve 20 may include a rigid or semi-rigid stent or be a so-called "stentless" type. In the illustrated embodiment, the heart valve 20 comprises a plurality of flexible leaflets 24 (typically three) that are mounted to a peripheral stent structure 26 and form fluid occluding surfaces within the valve orifice to form a one-way valve. The stent structure 26 includes a plurality of generally axially extending commissures 28 circumferentially distributed around the valve between and in the same number as the number of leaflets 24. Although not shown, additional components of the heart valve 20 typically include an inner stent and/or wireform support structure that provide a structural skeleton surrounding an inflow orifice and extending up the commissures 28. The inner components of the heart valve 20 may be made of suitable metal or plastic. As is well known, adjacent flexible leaflets 24 connect to and extend upward to meet along each of the commissures 28. In the illustrated embodiment, the structural components of the heart valve 20 support each flexible leaflet 24 along a valve cusp 30 and along two commissure 28 edges. A free edge 25 of each leaflet 24 extends inward toward a central flow orifice and coapts, or mates, with the free edges of the other leaflets, as shown. The valve orifice is oriented around an axis along an inflow-outflow direction through the valve. The valve commissures 28 project in the outflow direction, with the convex valve cusps 30 extending in the inflow direction between adjacent commissures. The bioprosthetic heart valves further includes a sewing ring 32 on the inflow end that conforms to the undulating contours of the valve cusps, or defines a generally circular, planar ring. The present application should not be considered limited to a particular valve construction unless explicitly stated herein.

The sealed conduit 22 defines a generally tubular structure that extends from an inflow end 42 to an outflow end 44. In the embodiment shown, the valve 20 is associated with the conduit 22 in such a way that the valve leaflets 24 control flow of blood through the conduit by permitting blood flow into the conduit (e.g., blood flow into the aorta, when the conduit is used for aortic replacement) while preventing flow of blood out of the conduit in the opposite direction (i.e., back into the left ventricle of the patient when used for aortic replacement).

The illustrated conduit 22 is particularly suited for attachment within the aortic annulus and ascending aorta, and as such closely matches the aortic root anatomy and includes an enlarged region or bulge 46 close to the inflow end 42 that conforms to the sinuses of valsalva just above the aortic annulus. In the preferred embodiment, the conduit 22 comprises a tubular textile structure, such as Dacron, sealed with a bioresorbable medium. A majority of the conduit 22 includes a corrugated (i.e., grooved) structure providing longitudinal flexibility and radial compressibility while ensuring that the conduit will not unduly radially expand under the pressure of blood flowing therethrough. The conduit 22 desirably has a length of from a few centimeters to 10-12 centimeters.

FIG. 1A illustrates a human heart H showing the valved conduit from FIG. 1 implanted above the left ventricle LV to replace the aortic valve and a portion of the ascending aorta AA. The surgeon sews the inflow end 42 to the aortic annulus, and the outflow end 44 to the remainder of the ascending aorta AA. Because the entire valve and a portion of the ascending aorta AA including the sinuses are removed, the two coronary arteries CA (one shown) attach at anastomoses AN to the enlarged region 46 of the conduit 22 between two of the three adjacent pairs of the commissures 28 of the valve 20. The bulged region 46 mimics the native sinuses and helps improve blood flow into the coronary arteries CA.

In one embodiment, the conduit 22 may be a Vascutek® Gelweave Valsalva™ Grafts gelatin sealed, aortic root graft that is indicated for aortic root replacement using valve sparing or replacement techniques, and available from the Vascutek business of Terumo Cardiovascular Systems Corporation of Ann Arbor, Mich. As explained below, the use of a bioresorbable medium to provide a temporary seal to the implanted graft is preferred and may be preassembled with the exemplary bioprosthetic heart valves disclosed herein. However, the exemplary bioprosthetic heart valves may also be pre-assembled with other sealed grafts or conduits, such as those that utilize non-bioresorbable material. It should be understood that unless excluded by claim language, a variety of sealed conduits are contemplated.

In the preferred embodiment, the sealed graft or conduit 22 is relatively impermeable in a dry state and immediately after implantation begins to become permeable. Such a response can be obtained by impregnating porous tubular structures with such materials as gelatin, collagen or albumin. A gelatin impregnated graft is not porous but when exposed to water the gelatin degrades by hydrolysis the rate at which hydrolysis proceeds being higher at the body temperature of 37° C. than it is at normal temperature. If the graft becomes porous at a rate too fast to keep pace with clotting and tissue growth, the gelatin may be treated in such a way as to cause cross links to form between the amino groups present in the gelatin molecules. Such cross linking renders the gelatin more resistant to hydrolysis and thus reduces considerably the rate at which the permeability of the graft increases. One method of initiating cross linking comprises exposing the gelatin to formaldehyde. The present application contemplates a conduit or graft which requires no pre-impregnation with blood and which after implantation starts to degrade and become permeable at an accurately known rate. It is to be understood that according to the medical circumstances of different implantations the porosity of the implanted grafts should increase at a rate only sufficient to avoid hemorrhage occurring. A method of producing a vascular graft according to these principles by impregnating a tube of flexible porous material with gelatinous material then treating the impregnated tube to cause only the amino groups always present in the molecules of gelatinous material to form cross links is disclosed in U.S. Pat. No. 4,747,848 to Maini, issued May 31, 1988, the contents of which are hereby expressly incorporated herein.

Figure 2A:
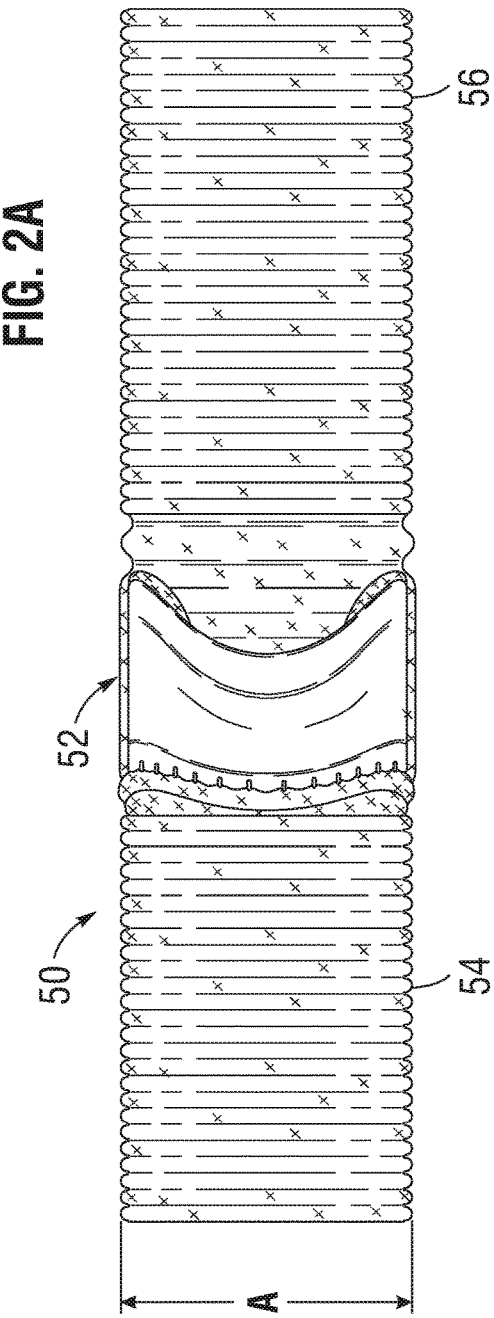
FIGS. 2A and 2B are side elevational views of an exemplary valved conduit of the present application wherein a bioprosthetic heart valve couples to two segments of sealed conduit extending from both ends thereof.
Figure 2B:
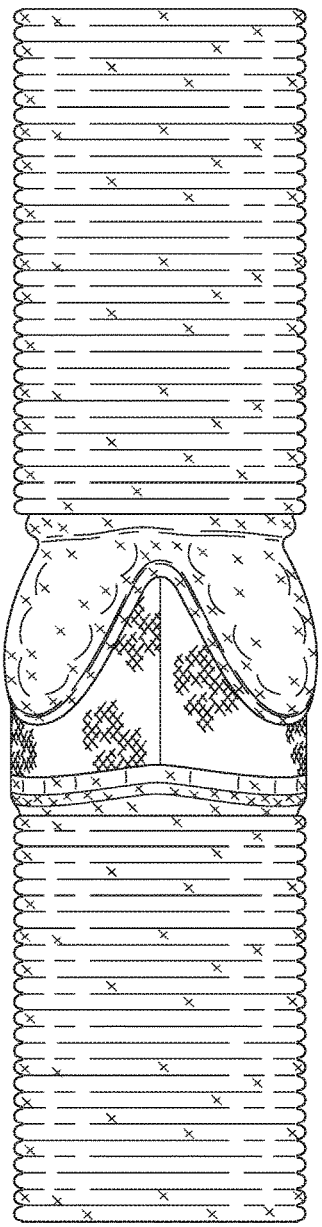

FIGS. 2A and 2B illustrate an alternative valved conduit 50 of the present application wherein a bioprosthetic valve 52 couples to two segments 54, 56 of sealed conduit extending from both ends thereof. The segments 54, 56 of sealed conduit comprise woven polyester sealed by techniques described above. The valved conduit 50 extends between an inflow end at the free end of the inflow segment 54 and an outflow end at the free end of the outflow segment 56. This construction can be utilized in a variety of locations within the body, including in the venous vasculature, as a bypass graft from the left ventricle to the descending aorta, or in the aortic annulus as described above. As such, the diametric sizes A of the valved conduit 50 can be as small as the smallest venous valves (2-5 mm) or as large as the largest heart valves (30 mm). A preferred diametric size ratio is between about 12-36 mm. An exemplary combination is a 29 mm valve connected to or within a 34 mm sealed conduit. Bioprosthetic heart valves with conduits are also used in the pulmonic position and in apical conduits. It should be noted that the bioprosthetic valve 52 illustrated is a bioprosthetic heart valve with three leaflets. Alternatively, the bioprosthetic valve 52 may be a bileaflet type, typical with venous valves.

The inflow and outflow segments 54, 56 are variable in length, and can be trimmed to size. Indeed, the two segments 54, 56 are typically trimmed close to the bioprosthetic valve 52. In the embodiment for use as a pulmonic valve replacement, the outflow segment 56 is approximately 50% longer than the inflow segment 54, such as 9 cm versus 6 cm. In one embodiment, the valved conduit 50 is constructed in the same manner as the Carpentier-Edwards® Bioprosthetic Valved Conduit available from Edwards Lifesciences of Irvine, Calif., though the conduit segments 54, 56 are preferably sealed with a bioresorbable medium such as gelatin or collagen. For an aortic valve replacement, the inflow extension segment 54 is not typically used, though a very short (<1 cm) inflow segment 54 can be provided, and the outflow segment 56 is preferably bulged, rather than being a straight tube as in FIGS. 2A/2B.

Figure 3:
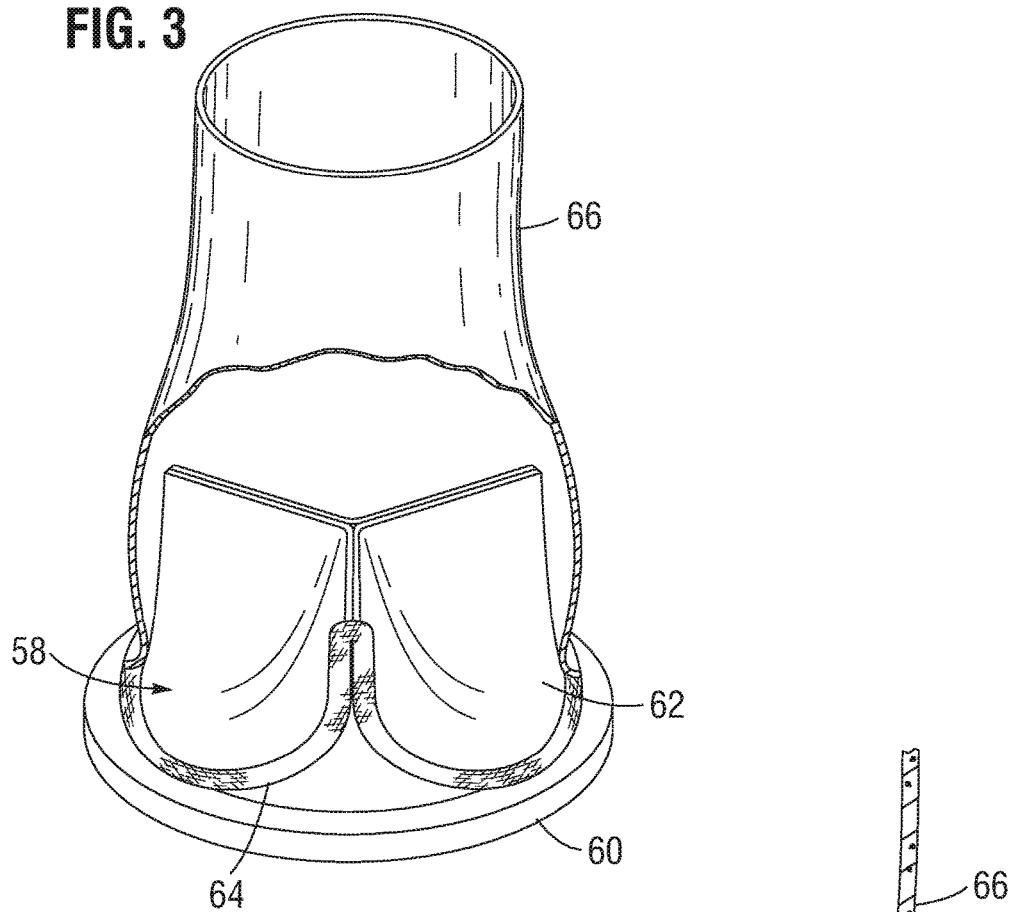
FIG. 3 is a still further view of a valved conduit with a bioprosthetic heart valve coupled within a sealed outflow conduit.

FIG. 3 is a still further view of a valved conduit with a bioprosthetic heart valve 58 coupled within a sealed outflow conduit 66. In some patients requiring replacement of the aortic valve, a portion of the aorta itself may be damaged or diseased such that it needs replacement as well, and the outflow conduit 66 functions to replace the damaged aorta. The bioprosthetic heart valve 58 is similar to that described above and includes flexible leaflets 62 supported by an undulating stent 64 having commissures. In contrast to the earlier valved conduit 20, the heart valve 58 couples to the outflow conduit 66 in a manner that the leaflets 62 are within the lumen of the conduit, while the sewing ring 60 of the valve is outside the conduit. This enables conventional attachment of the sewing ring 60 to the aortic annulus.

Figure 4B:
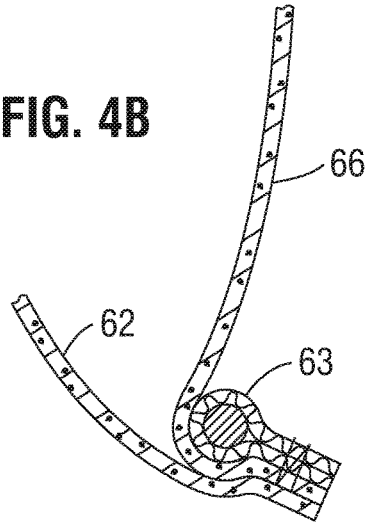
FIGS. 4A and 4B are enlarged cross-sectional views illustrating alternative techniques for attaching the outflow conduit to the bioprosthetic heart valve of FIG. 3.
Figure 4A:
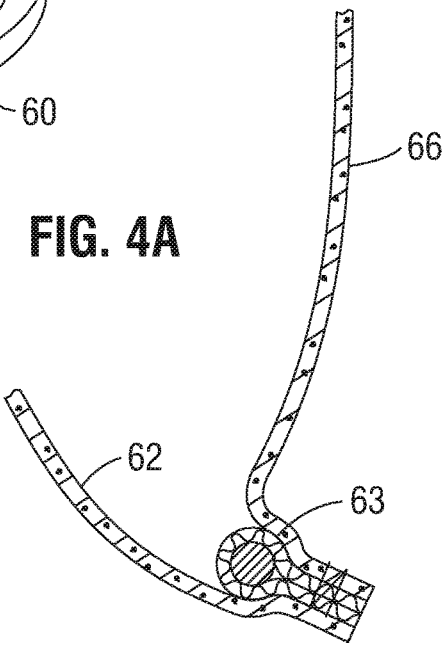

For example, FIGS. 4A and 4B illustrate techniques for attaching the outflow conduit 66 to the bioprosthetic heart valve 58. In both techniques, the outflow conduit 66 attaches to the cloth covering on a wireform 63 that forms a part of the stent 64 at the time that the tissue leaflets 62 are being secured. Referring to FIG. 4A, the conduit 66 may be secured on a side of wireform 54 opposite to tissue leaflets 62 by, for example, stitching. Alternatively, as shown in FIG. 4B, the conduit 66 may be stitched and secured to wireform 54 on the same side as tissue leaflets 62, or sandwiched therebetween. A third option is to simply secure conduit 66 to the periphery of the finished valve (not shown) as a subsequent sewing step. The valve 58 may be attached to an outflow conduit either with or without a sinus as shown. It should be noted that a short portion of the outflow conduit 66 that comes into direct contact with the leaflets 62 may be left free of a bioresorbable sealing medium to prevent any long-term reaction during storage between the medium and the bioprosthetic leaflets. Although FIGS. 4A and 4B are associated with the valved conduit 50 for aortic implant, the methods of construction are not preferred for a pericardial valve aortic conduit since the fabric of the conduit connected in abutment with the pericardial leaflets may cause abrasion of the leaflets and ultimately failure. However, such constructions may be suitable for porcine valve pulmonic conduits. Alternative construction techniques where the conduit attaches to the valve sewing ring are more desirable for aortic conduits with pericardial leaflet valves.

Figure 5:
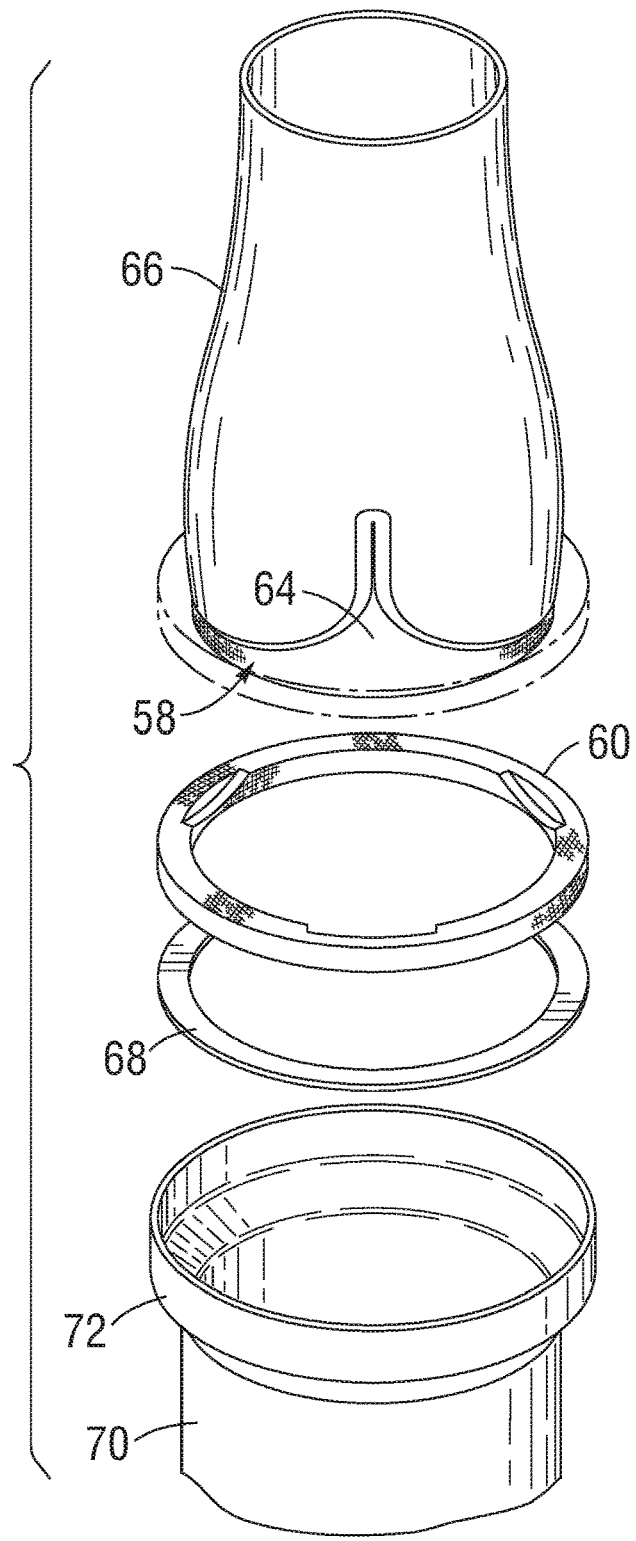
FIG. 5 is an exploded perspective view illustrating an additional application of the valved conduit the present application.

FIG. 5 is an exploded perspective view illustrating an additional application of a valved conduit including a modified bioprosthetic heart valve 58. Namely, in applications such as artificial hearts or left ventricular assist devices (LVADs), suture ring 60 is not necessarily required; hence, the lower end of stent 64 may be attached to a flange 68 for use in mounting the valve in an artificial heart or LVAD. Yet a further alternative adaptation involves those applications where an inflow conduit 70 is desired. In such applications, inflow conduit 70 may be attached directly to stent 64 of valve 58. More specifically, inflow conduit 70 may be configured to have a stepped circumference 72 that snugly mates with the outer periphery (or, alternatively, the inner periphery) of stent 64 and which can be sewn thereto. In this configuration, for example, in an artificial heart or an LVAD application, suture ring 60 could be attached to inflow conduit 70 rather than to valve 58.

The pre-assembled valved conduits disclosed herein each includes a bioprosthetic valve connected to a sealed conduit. The connection can be sewn within or to the end of the sealed conduit via sutures, as described above, or by a less time-consuming technique to limit handling of the two treated components and provide a hemostatic seal with minimal assembly complexity. For example, the bioprosthetic valve and conduit could be snapped together to minimize handling. Various potential snap mechanisms are disclosed in the art, including in U.S. Patent Publication No. 2006/0085060 to Campbell, the contents of which are hereby expressly incorporated herein. Snap together mechanisms could employ a wire, metal or plastic rings sewn into a proximal end of the conduit which would be captured by a metal or plastic ring surrounding the tissue valves. Alternatively, the conduit could be placed between an external ring and the bioprosthetic valve, or it could be snapped around the outside of the ring as long as the conduit did not block suture needles from being passed through the valve sewing ring.

Figure 6:
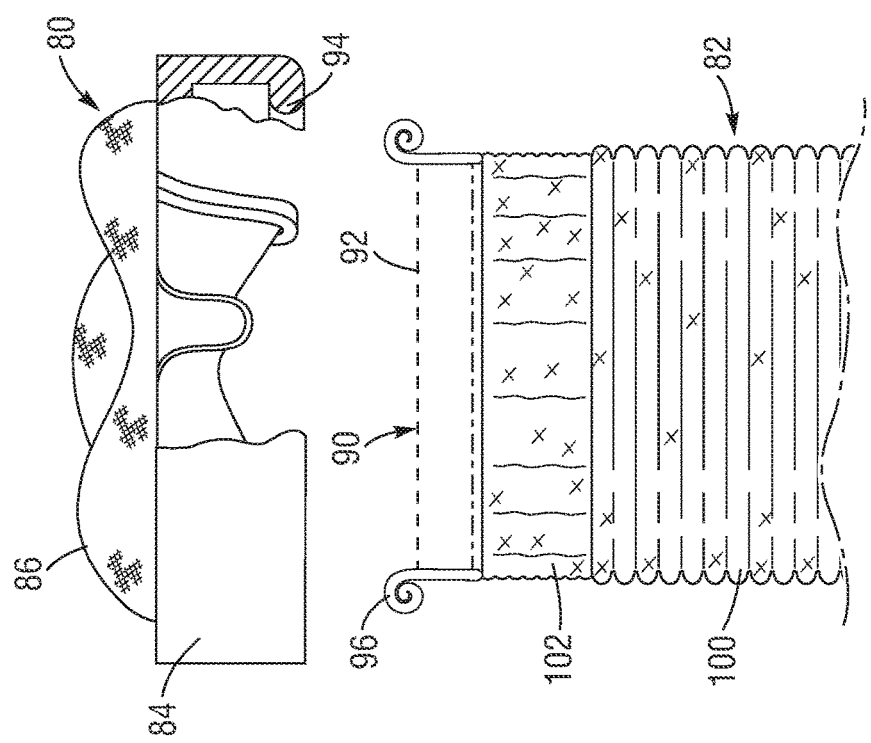
FIG. 6 is an exploded view of an exemplary snap-fit connection between a bioprosthetic heart valve (shown in partial section) and a sealed conduit.

FIG. 6 is an exploded view of an exemplary snap-fit connection between a bioprosthetic heart valve 80 and a sealed conduit 82. In particular, a coupling ring 84 attached to a sewing ring 86 of the valve 80 connects to an inflow end 90 of the sealed conduit 82. An inner periphery of the coupling ring 84 may be sewn or attached with barbs or the like to the sewing ring 86, and includes an open end surrounding the commissures 92 of the valve 80 with an inwardly projecting rim 94. The rim 94 mates with an outwardly projecting rim 96 on the inflow end 90 of the sealed conduit 82. It should be understood that the illustrated engagement between the coupling ring 84 and the inflow end of the conduit 82 is exemplary only, and representative of a variety of different such structures.

In an exemplary embodiment, the sealed conduit 82 has a tubular structure with a body portion 100 having a corrugated or pleated sidewall extending between the inflow end 90 and outflow and (not shown). The conduit 82 is desirably formed of a biocompatible fabric impregnated with a bioresorbable sealing medium such as gelatin or collagen. The corrugated or pleated sidewall provides longitudinal flexibility and radial compressibility while ensuring that the graft does not unduly radially expand under the pressure of blood flowing there through. The conduit 82 further includes an expandable portion 102 located between the body portion 100 and the inflow end 90. The expandable portion 102 may be formed of a material that is more radially expandable than the corrugated body portion 100 to allow expansion at that location into the Valsalva sinuses.

Figure 7:
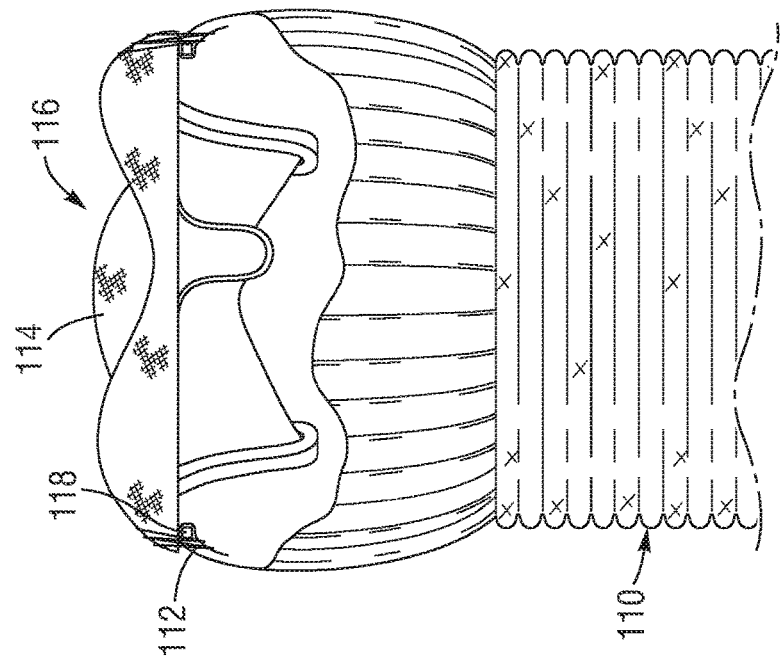
FIG. 7 is a sectional view of an exemplary sealed conduit connected with sutures to a sewing ring of a bioprosthetic heart valve.

FIG. 7 illustrates an exemplary sealed conduit 110 connected with sutures 112 to a sewing ring 114 of a bioprosthetic heart valve 116. A portion of the sealed conduit 110 wraps around and captures a resilient biocompatible band 118. In particular, the sutures 112 enclose the resilient band 118 in a pocket of the sealed conduit 110. The band 118 provides an added structural connection between the conduit 110 and valve 116 to prevent separation thereof, and as such may be made of a variety of biocompatible materials, including Elgiloy, titanium, or other such metals, or suitable polymers such as polypropylene.

Figure 8:
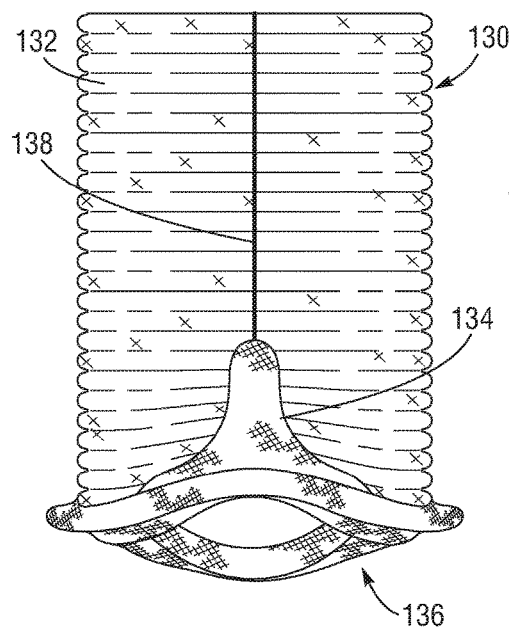
FIG. 8 is an elevational view of a valved conduit similar to that shown in FIG. 5 with a sealed conduit attached to a stent structure of a bioprosthetic heart valve.

FIG. 8 shows a valved conduit 130 similar to that shown in FIG. 5 with a sealed conduit 132 attached to a stent structure 134 of a bioprosthetic heart valve 136. In particular, an inflow end of the conduit 132 is sewn along an undulating path that follows the cusps and commissures of the stent structure 134. Axial marker lines 138 are provided on the conduit 132 to denote the three commissure post locations. This connection provides the advantage that a surgeon can easily see the commissure locations, but because the conduit is within the commissures the anastomotic attachment of coronary arteries is somewhat more difficult. Furthermore, as mentioned above for aortic pericardial conduits there is a greater possibility of leaflet abrasion.

Figure 9A:
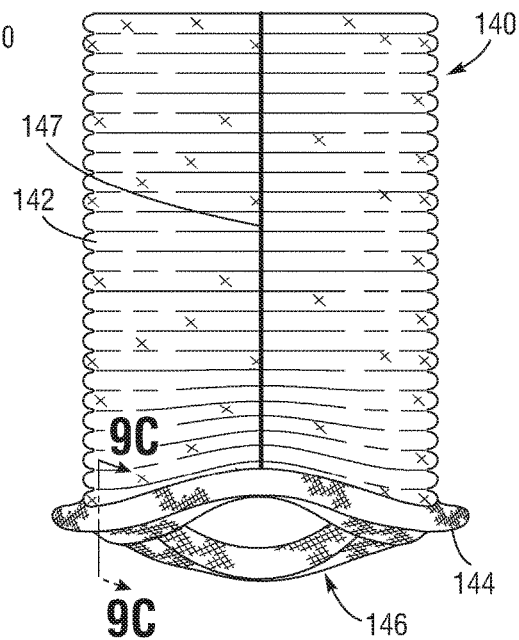
FIG. 9A is an elevational view of a valved conduit with a sealed conduit attached to a sewing ring of a bioprosthetic heart valve.
Figure 9B:
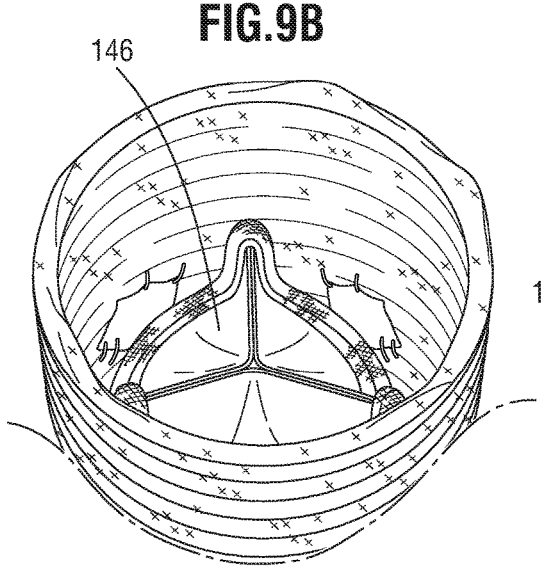
FIG. 9B is a perspective view of the valved conduit looking into an outflow end of the conduit.
Figure 9C:
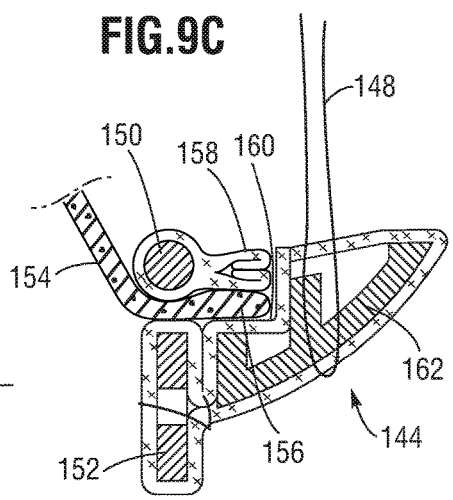
FIG. 9C is a sectional view through a cusp region of the heart valve in FIG. 9A showing one possible connection between the sealed conduit and the sewing ring.

FIGS. 9A and 9B on the other hand show a valved conduit 140 with a sealed conduit 142 attached to a sewing ring 144 of a bioprosthetic heart valve 146. The valve 146 is within the conduit 142 and axial marker lines 147 are provided on the conduit 142 to denote the three commissure post locations. FIG. 9C is a sectional view through a cusp region of the heart valve 146 schematically showing a suture loop 148 passing through the sewing ring 144 to connect the sealed conduit 142 to the sewing ring. The valve 146 has a cloth-covered wireform 150 that rests above a cloth-covered metallic or polymer stent 152, with a valve leaflet 154 sandwiched therebetween. A portion of the leaflet edge 156 and a flap 158 of the cloth around the wireform 150 extend outward onto a ledge 160 formed by a cloth-covered silicone waffle ring 162 that forms the sewing ring. The suture loop 148 passes through the entire waffle ring 162 and secures the inflow end of the sealed conduit 142 (not shown in FIG. 9C for clarity). This leaves an outer rim of the sewing ring 144 outside the conduit 142, as seen in FIG. 9A, through which anchoring sutures can be pre-threaded for parachuting the valved conduit 140 down to the target annulus.

Figure 10:
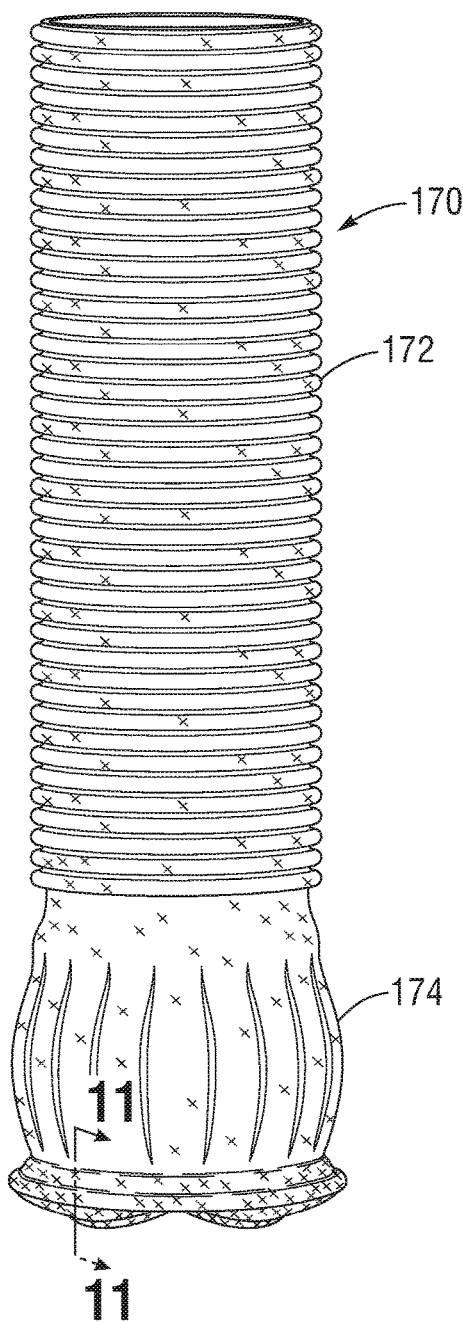
FIG. 10 is an elevational view of a valved conduit similar to that shown in FIG. 9A with a longer sealed conduit having a sinus region attached to a sewing ring of a bioprosthetic heart valve.
Figure 11A:
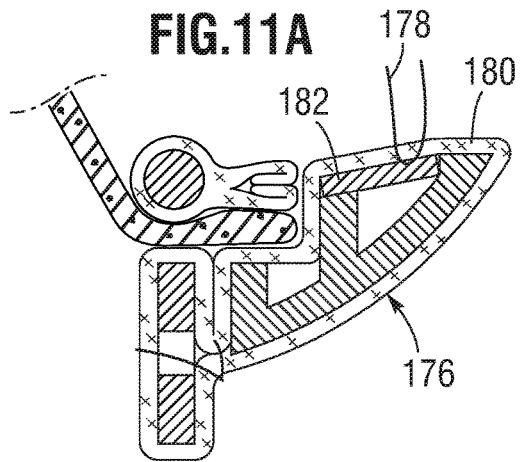
FIGS. 11A-11C are sectional views through a cusp region of the heart valve in FIG. 10 showing possible connections between the sealed conduit and the sewing ring.
Figure 11B:
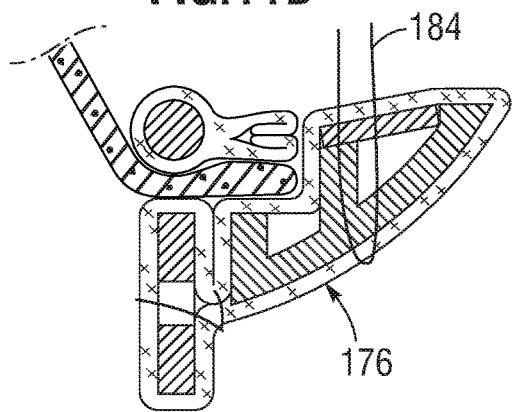
Figure 11C:
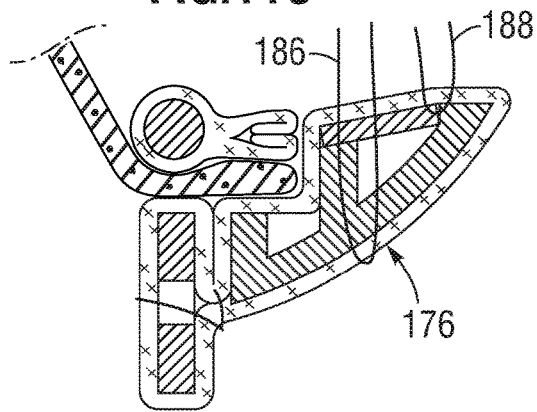

FIG. 10 shows a valved conduit 170 similar to that shown in FIG. 9A with a longer sealed conduit 172 having a sinus region 174 attached to a sewing ring 176 of a bioprosthetic heart valve (not visible). FIGS. 11A-11C are sectional views through a cusp region of the heart valve in FIG. 10 showing possible connections between the sealed conduit 172 (not shown for clarity) and the sewing ring 176. FIG. 11A shows a suture loop 178 passing just through an upper cloth layer 180 of the sewing ring 176, or through a supplemental upper ring washer 182 formed of a polymer such as Nylon, which is sometimes used in sewing rings. FIG. 11B shows a suture loop 184 extending the entire axial height of the sewing ring 176, much like in FIG. 9C. Finally, FIG. 11C shows two loops 186, 188 passing through the entire sewing ring 176 as well as just through an upper cloth layer 180 for added security.

Figure 12:
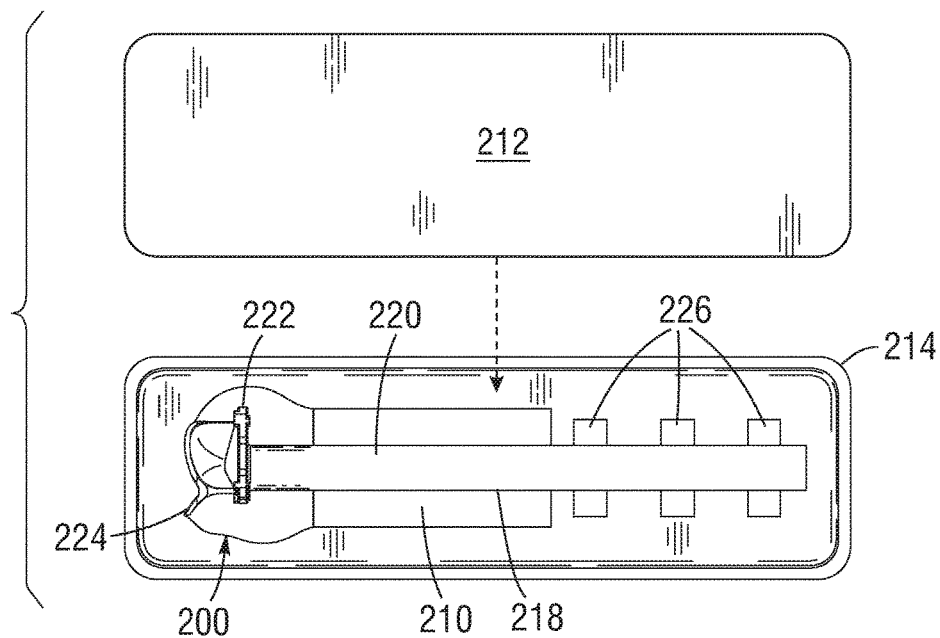
FIG. 12 is an exploded plan view of a valved conduit and holder therefore mounted in a primary storage container in the form of a tray.

FIG. 12 illustrates an exemplary primary storage container for a valved conduit 200 of the present application. The primary storage container comprises a molded storage tray 210 and a sheet-like gas-permeable lid 212. In particular, the assembled valved conduit 200 is placed within a cavity of the storage tray 210, whereupon the lid 212 is adhered to an upper rim 214 of the tray. The upper rim 214 defines the tray upper surface, and the process of adhering the lid 212 to the rim 214 can be performed easily using automated equipment. The adhesive may be provided on the upper rim 214, or on the underside of the lid 212.

In a preferred embodiment, features provided in the cavity of the tray 210 secure the valved conduit 200 from movement therein, and prevent a sealed conduit 218 from touching any inner surfaces of the tray. The bioresorbable sealing medium in the sealed conduit 218 can abrade if permitted to touch the inside of the tray during handling, potentially degrading its sealing capability. For example, a valve holder 220 may be attached to commissure posts of the heart valve 222, and an elongated delivery handle 224 extends from the holder out of an outflow end 226 of the sealed conduit 218. A series of cooperating brackets 226 firmly holds the handle 224 in position in the tray 210, while the valved conduit 200, and in particular the sealed conduit 218, is suspended within an enlarged cavity (not shown) of the tray. Because the tray 210 secures the components in this manner, the valved conduit 200 is stably suspended within the cavity without touching the sides of the tray 210.

Preferably, the lid 212 is closely dimensioned to the perimeter of the upper rim 214, and the band of adhesive is a pressure-seal or a heat seal adhesive to facilitate sealing under pressure and/or temperature. The material of the lid 212 is breathable, or gas-permeable, to permit gas sterilization of the contents sealed within the tray 210, in particular the dry tissue heart valve of the valved conduit 200. One suitable gas-permeable material is a sheet of high-density polyethylene fibers, which is difficult to tear but can easily be cut with scissors. The material is highly breathable and water vapor and gasses can pass through the fibers, but not liquid water. For instance, various Tyvek materials from DuPont may be used. Also, exemplary hot-melt adhesives used to secure the lid 212 to the tray 210 may be obtained from Perfecseal or Oliver-Tolas, for example. Such a material permits sterilization of the tray contents using Ethylene Oxide (ETO), which gradually passes through the lid 212 to the interior tray. The lid 212 presents a sterile barrier and prevents ingress of microorganisms. The tray 210 is a gas-impermeable molded material, such as a polyethylene terephthalate copolymer (PETG). Various medical storage materials and packaging suitable for assembly of components of the present application are available from companies such as Dupont, Perfecseal, Oliver-Tolas, and Mangar. Other means of sterilization include gamma irradiation or electron beam irradiation.

Ethylene oxide (ETO), also called oxirane, is the organic compound with the formula $C_2H_4O$. It is commonly handled and shipped as a refrigerated liquid. ETO is often used as sterilant because it kills bacteria (and their endospores), mold, and fungi. It is used to sterilize substances that would be damaged by high temperature techniques such as pasteurization or autoclaving. Ethylene oxide is widely used to sterilize the majority of medical supplies such as bandages, sutures, and surgical implements in a traditional chamber sterilization method, where a chamber has most of the oxygen removed (to prevent an explosion) and then is flooded with a mixture of ethylene oxide and other gases that are later aerated.

Certain features of the tray 210 facilitate gas sterilization, such as with ETO, though other means such as gamma irradiation or electron beam irradiation could be used. Specifically, the tray 210 retains the valved conduit 200 securely therein but provides adequate channeling in and around the components to eliminate any enclosed spaces. The sterilization gas can therefore flow evenly throughout the entire enclosure.

One advantage of the packaging solutions described herein is a double sterile barrier, wherein the inner and outer sterile containers allow for gas sterilization, such as with ETO, and with a second seal the outer sterile container also provides an oxygen barrier to the product after sterilization. The inner sterile container has been described above with reference to FIG. 12 in the form of a storage tray 210 sealed with the lid 212. The sealed storage tray 210 is received within a secondary or outer container and the dual barrier assembly is then sterilized, so that there are redundant sterile barriers. Subsequently, the dual barrier assembly is sealed to prevent oxygen from reaching the valved conduit 200, thus preventing oxygenation and potentially reducing calcification after implant. In the exemplary packaging sequence, the primary and secondary containers are first assembled together and each closed with a gas-permeable barrier to form a dual barrier assembly which is gas-sterilized. Subsequently, the oxygen barrier is added, such as by converting the secondary container from being gas-permeable to being gas-impermeable. However, if the entire process is done in sterile conditions, such as in a clean room environment, the primary container may be closed and sterilized before being placed within the secondary container, which is then closed and sterilized. In other words, there may be one or two sterilization steps prior to sealing the entire assembly against oxygen ingress.

Desirably, a desiccant is used within the inner and/or the outer packaging layers. For instance, a desiccant pouch may be inserted with the valved conduit 200 into the inner package, to absorb any residual water vapor trapped therein when the gas-permeable tray lid 212 is closed. A second desiccant pouch may be inserted between the inner and outer barriers to absorb any residual water vapor therein, or it may be the only desiccant pouch used.

The present application describes two different secondary barriers—one a storage tray described below, and the other a flexible pouch. The secondary barrier protects and preserves the primary sterile barrier package in a sterile environment, and prevents oxygen from reaching the heart valve of the valved conduit 200 within. A further outer shelf box may be used to facilitate temperature monitoring during distribution and storage, and protect the delicate implant from distribution hazards such as shock, impact and extreme temperatures.

Figure 13:
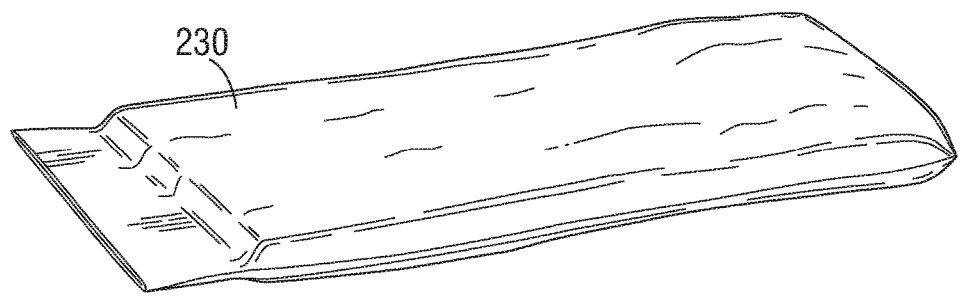
FIG. 13 is a perspective view of the valved conduit in the tray as in FIG. 12 contained within a secondary storage container in the form of a pouch.

FIG. 13 is a perspective view of the valved conduit 200 in the primary storage tray 210 with the lid 212 attached (all not shown), as in FIG. 12, and then contained within a secondary storage container in the form of a pouch 230. Desirably, the storage pouch 230 includes a dual seal system on its open end which provides both a gas-permeable portion and a gas-impermeable portion, depending on which seal is closed.

Figure 14:
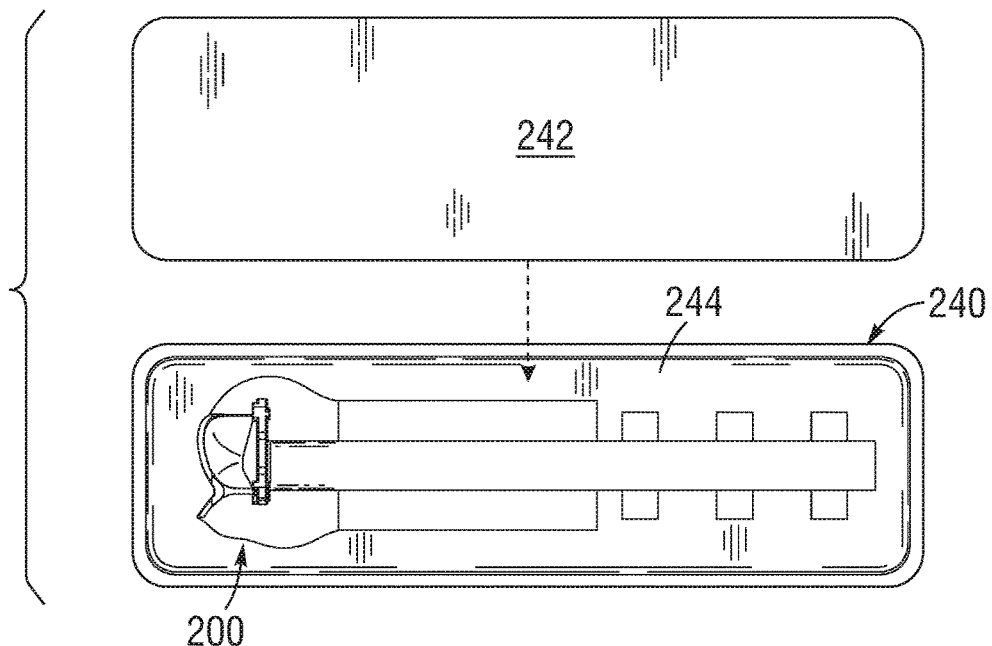
FIG. 14 is an exploded plan view of the valved conduit of FIG. 10 mounted in an exemplary primary storage container in the form of a tray.

FIG. 14 illustrates the valved conduit 220 mounted in an exemplary primary storage container in the form of a tray 240 and a sheet-like gas-permeable lid 242. The tray 240 features cavities for the valved conduit 220 which retain and stabilize the components therein. The lid 242 adheres to an upper rim 244 of the tray 240.

Figure 15:
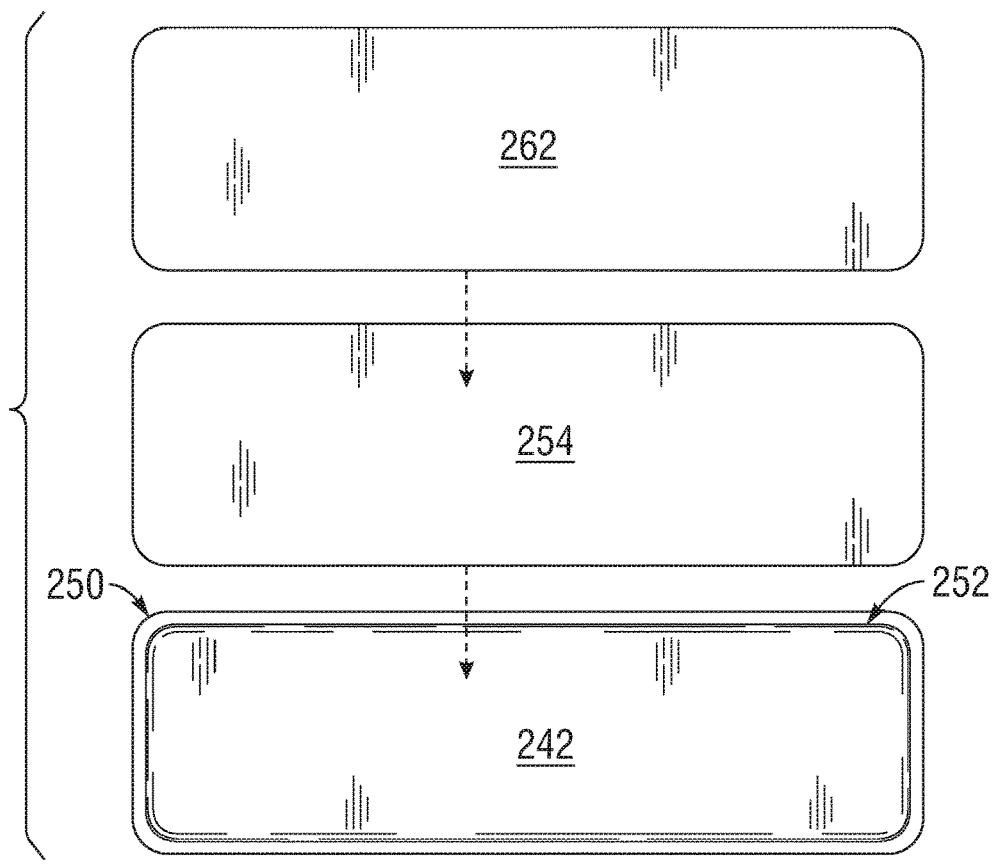
FIG. 15 is an exploded plan view of the valved conduit of FIG. 10 in the tray as in FIG. 14 contained within a secondary storage container in the form of an outer tray.

FIG. 15 illustrates the valved conduit 220 in the tray (of which the lid 242 is seen) as in FIG. 14, and then placed within a secondary storage container in the form of an outer or secondary tray 250 for a dual-barrier packaging system. The secondary storage tray 250 desirably mimics the shape of the primary storage tray 240 such that the latter can be easily nest within a cavity formed therein. The secondary storage tray 250 comprises an upper surface including a peripheral flange 252.

The outer storage tray 250 provides a rigid secondary sterile barrier that protects and preserves the inner sterile barrier formed by the inner storage tray 240 and its lid 242. The outer storage tray 250 may be constructed of a gas-impermeable molded material, such as a polyethylene terephthalate copolymer (PETG). Once the sealed inner tray 240 is placed within the outer storage tray 250, a gas-permeable lid 254 seals against the flange 252 and permits sterilization gas (e.g., ETO) to reach the spaces within both trays.

Subsequently, a gas-impermeable label 262 sized to cover the secondary storage tray 250 is shown. The label 262 is applied over the sterilized tray 250, and sealed on top of the lid 254. Once pressure adhered or heat sealed against the lid, the label 262 provides a complete barrier to gas transfer. The label 262 preferably includes a layer of metal foil laminated to a layer of a gas-permeable material such as DuPont 1073B Tyvek, or more preferably is a single layer of foil. The label 262 may have information printed thereon about the contents of the packaging, such as implant type, model, manufacturer, serial number, date of packaging, etc. A layer of pressure sensitive adhesive is provided to seal on top of the previously attached lid 254.

Alternatively, the secondary storage tray 250 features a double flange (not shown) around its upper edge. An inner flange may first be sealed with a die-cut and heat seal adhesive coated gas-permeable lid (e.g., Tyvek), such as lid 254, after placement of the inner sterile barrier package, enabling subsequent ETO sterilization of the entire package, and in particular the space between the two sterile barriers. A gas-impermeable label such as the foil label 262 is then sealed to an outer flange.

The packaging solutions disclosed herein facilitate access to the valved conduits at the time of implantation. The process for removing the valved conduit 220 from its packaging will be described, though similar steps can be used to remove the other valved conduits. The first step is removal of the outer or secondary sterile barrier (pouch or tray). This description will assume a secondary storage tray 250. One or both sealed labels over the outer tray 250 are first detached, and the inner tray 240 sealed by a sterile lid 242 removed therefrom (alternatively, the technician tears open a sterile pouch). At this stage, the inner sterile packaging may be transported to the immediate vicinity of the operation site without undue concern for the integrity of the package because of the relatively rigid inner tray 240 and sterile seal 242.

Subsequently, the technician detaches the lid 242, exposing the valved conduit 220. The valved conduit 220 is then removed from the packaging and implanted according to various procedures.

The preferred dual-barrier packaging system provides a number of distinctive advantages to manufacturers of the valved conduits of the present application. Due to presence of a gas-permeable sterile barrier such as a Tyvek Header (breathable vent) the product can easily be ETO sterilized and aerated for acceptable levels of residuals. After appropriate aeration time, the outer container, or second barrier, can be sealed (e.g., foil to foil) to prevent long term oxidation of the dry tissue valve. The ETO sterilization obviates traditional oven sterilization, therefore reducing the amount of energy spent in heating the packaged product in an oven for multiple days. Similarly, elimination of autoclaving before packaging will reduce the energy consumption required in the sterilization process.

As mentioned, the double sterile barrier allows for gas sterilization, such as with ETO, but also provides an oxygen barrier to the product after sterilization. Consequently, the entire assembly can be reliably stored in oxygen-free conditions for extended periods of time, even years, yet the outer sterile container can be removed at the time of use without exposing the contents of the inner sterile container to contaminants. The double layer of packaging enables sterile transfer of the inner package to the sterile operating field, and the inner package can even be temporarily stored for significant periods before the product is used. The new package design will be lighter in weight due to the choice of materials (PETG/Tyvek and air vs. Polypropylene with glutaraldehyde), which will reduce the shipping costs for single unit shipments.

Indeed, the biggest advantage over existing "wet" heart valve package designs is the elimination of storage and handling of liquid glutaraldehyde during the packaging and storage process, as well as the absence of glutaraldehyde at the time of use. This reduces hazards to the health of employees, customers, and patients, as well as the environment. Additionally, disposal of glutaraldehyde is bio-hazardous and therefore OSHA requires neutralization of the chemical before disposal or placement of appropriate controls for disposal. Due to decreased handling and critical storage requirements described herein, the packaging process is rendered less complex. The elimination of glutaraldehyde will not require an increased level of insulation from higher temperatures as the dry tissue valve already has the capability to withstand temperatures as high as 55° C. The replacement of water with glycerin also provides protection from freezing down to a temperature of −18° C. Therefore this will likely reduce the bulkiness of the design by reducing the size and insulation used for shipping the valve during summers and winters.

The packaging provided for the various valved conduits desirably incorporate some means within to maintain a predetermined low humidity level. The valved conduits which include bioresorbable materials, in particular gelatin, may hydrolyze faster in the body if they are stored in excessively moist conditions. Typically, sealed conduits with a bioresorbable sealing medium are stored with desiccant pouches to maintain extremely dry conditions. However, the bioprosthetic valves disclosed herein, although stored dry, must retain a certain amount of moisture to remain functional. In one embodiment, a desiccant pouch is provided within the packaging having a capacity for absorbing moisture within the packaging limited to avoid drying the bioprosthetic tissue out beyond a point where its ability to function in the bioprosthetic heart valve is compromised. In short, the two components of the valved conduits described herein have slightly different needs when it comes to the moisture content of the shipping package.

While the invention has been described in its preferred embodiments, it is to be understood that the words which have been used are words of description and not of limitation. Therefore, changes may be made within the appended claims without departing from the true scope of the invention.

What is claimed is:

1. A pre-assembled valved conduit, comprising:
   a bioprosthetic heart valve including bioprosthetic tissue leaflets, the valve having been treated such that the tissue may be stored dry for extended periods without degradation of functionality of the valve, the bioprosthetic valve having a sewing ring encircling an inflow end, wherein the tissue leaflets are supported by three commissure posts evenly located around the valve that project in an outflow direction, with three convex valve cusps therebetween extending in an inflow direction;
   a conduit sealed with a bioresorbable medium that is coupled to the sewing ring with sutures so as to form the valved conduit including three axial marker lines provided on an exterior of the conduit aligned with and signifying the locations of the three commissure posts;
   a valve holder attached to the bioprosthetic valve on an outflow side of the valve cusps; and
   an elongated delivery handle connected to the valve holder and extending through the conduit so as to project from an outlet end thereof.

2. The valved conduit of claim 1, wherein the heart valve is located at an inlet end of the conduit that wraps around the sewing ring.

3. The valved conduit of claim 2, wherein the sutures coupling the conduit inlet end to the sewing ring pass through the entire sewing ring from inflow to outflow sides thereof.

4. The valved conduit of claim 1, wherein the heart valve includes bovine pericardial leaflets, and the conduit comprises a tubular matrix impregnated with gelatin or collagen.

5. The valved conduit of claim 1, wherein the bioprosthetic valve couples within the conduit such that the conduit extends on both ends of the valve to provide both inflow and outflow extensions.

6. The valved conduit of claim 1, wherein the bioprosthetic tissue leaflets have been cross-linked using glutaraldehyde or other aldehyde containing agents, treated with a capping agent, and dehydrated with a glycerol solution.

7. A packaged pre-assembled valved conduit, comprising:
   a pre-assembled valved conduit including a bioprosthetic valve with bioprosthetic tissue leaflets, the valve having been treated such that the tissue may be stored dry for extended periods without degradation of functionality of the valve, the bioprosthetic valve being coupled to a conduit sealed with a bioresorbable medium;
   a valve holder attached to the bioprosthetic valve on an outflow side thereof; and
   an elongated delivery handle connected to the valve holder and extending through the conduit so as to project from an outlet end thereof; and
   packaging for the valved conduit including at least one sterile container in which the valved conduit, holder and handle are stored assembled without a preserving solution.

8. The packaged pre-assembled valved conduit of claim 7, wherein the packaging comprises a dual layer packaging with the valved conduit sealed within an inner gas-permeable sterile barrier to enable gas sterilization and an outer gas-impermeable barrier to prevent long term oxidation of the bioprosthetic tissue.

9. The packaged pre-assembled valved conduit of claim 8, wherein the outer gas-impermeable barrier comprises a storage pouch having a dual seal system on its open end which provides both a gas-permeable portion and a gas-impermeable portion.

10. The packaged pre-assembled valved conduit of claim 7, wherein the conduit comprises a tubular matrix impregnated with gelatin, and further including a desiccant pouch provided within the packaging having a capacity for absorbing moisture within the packaging limited to avoid drying the bioprosthetic tissue out beyond a point where its ability to function as a bioprosthetic valve is compromised.

11. The packaged pre-assembled valved conduit of claim 7, wherein the bioprosthetic tissue leaflets have been crosslinked using glutaraldehyde or other aldehyde containing agents, treated with a capping agent, and dehydrated with a glycerol solution.

12. A pre-assembled valved conduit, comprising:
a bioprosthetic valve including bioprosthetic tissue leaflets cross-linked using glutaraldehyde or other aldehyde containing agents, treated with a capping agent, and dehydrated with a glycerol solution such that the tissue leaflets may be stored dry for extended periods without degradation of functionality of the valve, the bioprosthetic valve having a sewing ring encircling an inflow end;
a conduit sealed with a bioresorbable medium that is coupled to the sewing ring with sutures so as to form the valved conduit;
a valve holder attached to the bioprosthetic valve on an outflow side thereof; and
an elongated delivery handle connected to the valve holder and extending through the conduit so as to project from an outlet end thereof.

13. The valved conduit of claim 12, wherein the bioprosthetic valve is a heart valve located at an inlet end of the conduit that wraps around the sewing ring.

14. The valved conduit of claim 12, wherein the bioprosthetic valve couples within the conduit such that the conduit extends on both ends of the valve to provide both inflow and outflow extensions.

15. The valved conduit of claim 12, further including packaging for the valved conduit including at least one sterile container in which the valved conduit, holder and handle are stored assembled without a preserving solution.

16. The valved conduit of claim 15, wherein the packaging comprises a dual layer packaging with the valved conduit sealed within an inner gas-permeable sterile barrier to enable gas sterilization and an outer gas-impermeable barrier to prevent long term oxidation of the bioprosthetic tissue.

17. The valved conduit of claim 15, wherein the conduit comprises a tubular matrix impregnated with gelatin, and further including a desiccant pouch provided within the packaging having a capacity for absorbing moisture within the packaging limited to avoid drying the bioprosthetic tissue out beyond a point where its ability to function as a bioprosthetic valve is compromised.

* * * * *